United States Patent

Attridge et al.

[11] Patent Number: 5,994,091
[45] Date of Patent: Nov. 30, 1999

[54] OPTICAL SENSOR FOR ENZYME AND ENZYME SUBSTRATES

[75] Inventors: John Worthington Attridge, Woking; Grenville Arthur Robinson, London, both of United Kingdom

[73] Assignee: Applied Research Systems ARS Holding N.V., Netherlands Antilles

[21] Appl. No.: 08/779,201

[22] Filed: Jan. 6, 1997

Related U.S. Application Data

[63] Continuation of application No. 08/351,325, filed as application No. PCT/GB93/01216, Dec. 12, 1994, abandoned.

[30] Foreign Application Priority Data

Jun. 10, 1992 [GB] United Kingdom ................. 92123058

[51] Int. Cl.$^6$ .................................................. G01N 33/53
[52] U.S. Cl. ...................... 435/7.72; 435/14; 435/287.9; 435/288.7; 422/82.11
[58] Field of Search ................... 435/4, 14, 287.9, 435/288.7; 204/403; 250/343; 422/82.08, 82.11

[56] References Cited

U.S. PATENT DOCUMENTS

| Re. 33,064 | 9/1989 | Carter | 436/34 |
|---|---|---|---|
| 4,880,752 | 11/1989 | Keck | 435/7 |
| 4,889,407 | 12/1989 | Markle et al. | 350/96.29 |
| 4,978,503 | 12/1990 | Shanks | 422/58 |
| 5,192,802 | 3/1993 | Attridge | 422/57 |
| 5,300,779 | 4/1994 | Hillman | 250/341 |

FOREIGN PATENT DOCUMENTS

| 75353 | 3/1983 | European Pat. Off. . |
| 171148 | 2/1986 | European Pat. Off. . |
| 175585 | 3/1986 | European Pat. Off. . |
| 9110757 | 2/1992 | Germany . |
| 9014590 | 11/1990 | WIPO . |
| 9221768 | 12/1992 | WIPO . |

OTHER PUBLICATIONS

Patent Abstracts of Japan, vol. 14, No. 21 (P-990) Jan. 17, 1990 & JP A 12 63 537 (NOK Corp.) Oct. 20, 1989.

*Primary Examiner*—David A. Redding
*Attorney, Agent, or Firm*—Ostrolenk, Faber, Gerb & Soffen, LLP

[57] ABSTRACT

Sensor devices for use in assaying for a substance selected from (i) enzymes capable of producing a change in their environment as a result of catalytic reaction with a substrate and (ii) substrates for such enzymes is described, the devices comprising an optical waveguide having immobilized directly or indirectly on a discrete region ("the measurement region") of one longitudinal surface thereof a species whose optical properties change as a result of the aforementioned change in its environment together with the member of an enzyme substrate/enzyme pair complementary to the substance under assay. Methods of assay using such devices are also described.

11 Claims, 4 Drawing Sheets

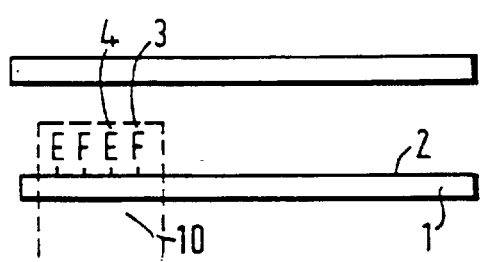
FIG.3a.
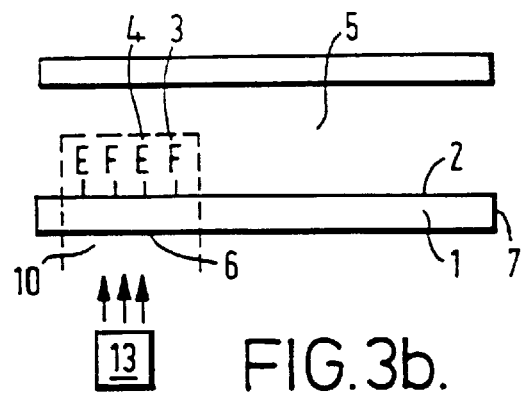
FIG.3b.
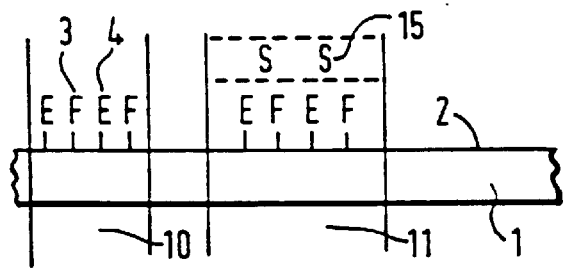
FIG.4a.
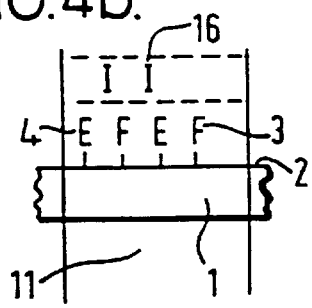
FIG.4b.
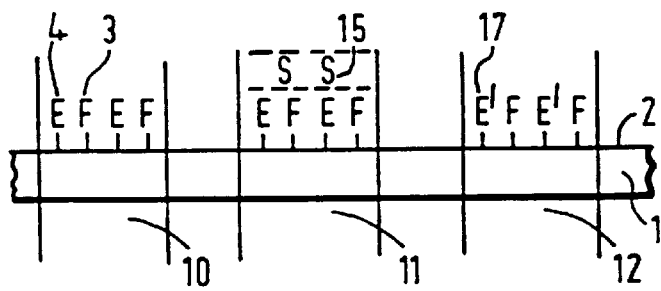
FIG.4c.
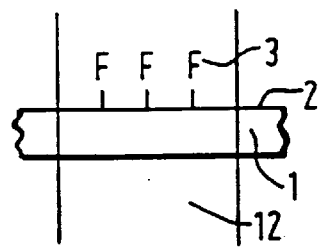
FIG.4d.
FIG.4e.
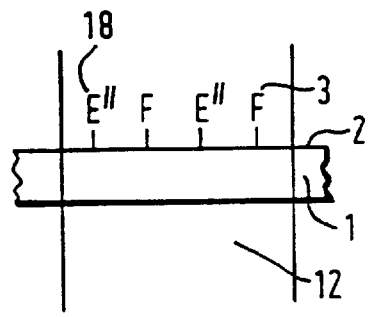
FIG.4f.
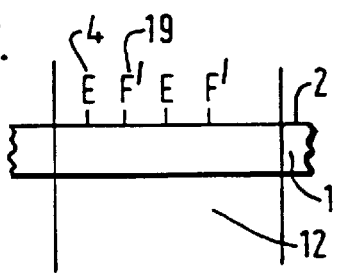

OPTICAL SENSOR FOR ENZYME AND ENZYME SUBSTRATES

This is a Continuation of application Ser. No. 08/351,325 filed on Dec. 12, 1994, now abandoned, which is a 371 of PCT/GB93/01216, filed Jun. 9, 1993.

This invention relates to a device for use in the assay of chemical or biochemical entities, and in particular to a biosensor for the detection of enzymes or enzyme substrates.

Enzyme-based sensors (enzyme electrodes) have previously been produced for the detection of a wide variety of analytes, one instance being sensors for the measurement of blood-gas concentrations (Clarke and Lyons, Annals of the New York Academy of Science, Vol. 102, pp 29–45, 1962). Many such biosensors employ an enzyme whose catalytic reaction results in a pH change which is recorded using either amperometric or potentiometric electrodes. The concentration of the analyte of interest is monitored by studying the rate of change or the absolute change in pH. To improve both the analytical performance and operational stability of such devices, the enzyme is frequently immobilised behind a semi-permeable membrane at the surface of the pH electrode. Analytes studied in this way include penicillin (Guilbault, G. G, Handbook of Immobilised Enzymes, Marcel Dekker, New York, 1984) and glucose (Clarke and Lyons, 1962). Advances in the field of microelectronics led to attempts to miniaturise these pH based enzyme sensor electrodes, substituting the conventional macro-pH electrode with a very much smaller pH sensitive ion selective field effect transistor (ISFET). Sensors for penicillin and glucose have been fabricated using such technology and are reviewed in the literature (Biosensors: Fundamentals and Applications, edited by A. P. F. Turner, I. Karube, G. S. Wilson, Oxford Scientific Publications, 1987).

However, such potentiometric systems suffer from a number of disadvantages; for example they are prone to electrical noise and interference due to other ions present in the sample. Attempts have therefore been made to fabricate the equivalents of such devices for use in optical technology.

A sensor for penicillin has been reported (Kulp T. J. et al, Analytical Chemistry, Vol. 59, pp 2849–2853 1987) which employs an optical fibre, the end of which is coated with a polymer into which is incorporated or to which is bound a penicillinase and a pH-dependent fluorescent dye. As the enzyme reacts with its substrate, the change in optical properties of the dye is measured and this change gives a measurement of the substrate concentration. Such a device, however, suffers from a number of disadvantages, in particular a difficulty associated with its fabrication which requires the immobilisation of a substantial mass of enzyme and dye on the end of the fibre to achieve a sufficiently sensitive assay. In use, difficulties also arise from optical interference from the sample, for example due to sample fluorescence and turbidity.

The present invention provides an enzyme-based optical biosensor which overcomes many of the disadvantages of the potentiometric pH sensors and the optical fibre sensor described above.

According to one aspect of the present invention, there is provided a sensor device for use in assaying for a substance selected from (i) enzymes capable of producing a change in their environment as a result of catalytic reaction with a substrate and (ii) substrates for such enzymes, which sensor device comprises an optical waveguide having immobilised directly or indirectly on a discrete region ("the measurement region") of one longitudinal surface thereof a species whose optical properties change as a result of the aforementioned change in its environment together with the member of an enzyme substrate/enzyme pair complementary to the substance under assay.

In the case of an enzyme for which a cofactor is necessary for said catalytic reaction to occur, the cofactor can also be present in the device or the cofactor can be supplied separately.

According to a further aspect of the present invention, there is provided a method of assay for an enzyme or an enzyme-substrate in a sample which method includes the steps of:

(a) incubating the sample in the presence of a device according to the invention as hereinbefore defined;

(b) irradiating the device;

(c) monitoring an appropriate optical property ("the measurement signal") thereby exhibited by the species in said measurement region of said device;

(d) determining whether and, if desired, the extent to which and/or the rate at which the said optical property is altered by any change in the environment in said measurement region; and (e) using an appropriate algorithm, determining any corresponding change in the environment in said measurement region caused by any interaction of enzyme and enzyme-substrate and thereby deriving a measure of the concentration of the analyte under assay.

Where a cofactor is necessary for said catalytic reaction to occur, if the cofactor is not already present in or on the device, then it should be introduced into the sample prior to, during or subsequent to the incubation in step (a) above.

A wide variety of sensors according to the present invention may be envisaged including, for example, dipstick or 'test-strip' biosensors, devices using a 'sample flow-through' configuration or devices employing sample containment, for example capillary fill devices of the type generally described in EP 171148.

Any enzyme which produces a change in its environment as a result of its catalytic activity is suitable for use in the device. Of particular note are enzymes which produce a pH change as a result of their catalytic activity, for example, penicillinase, glucose oxidase or urease. Many other changes are possible and, include a change (increase or decrease) in the oxygen concentration in the solution concerned, for example using glucose oxidase which consumes oxygen as a result of its catalytic activity, or the use of a peroxidase which produces hydrogen peroxide as a result of its catalytic activity.

The species whose optical properties change as a result of a change in its environment may, for example, be a fluorophore or dye sensitive to the change concerned. Examples of preferred pH-sensitive species include fluorescein isothiocynate (FITC), fluoresceinamine and fluorescein iodoacetamide. A preferred species sensitive to the oxygen concentration in its environment is FITC. Several fluorescent species are sensitive to the $H_2O_2$ concentration in their environment.

Devices according to the invention find particular use in assays in which detection of the change in optical properties of a fluorophore or dye is effected by means of techniques involving the phenomenon of evanescent wave coupling. Such techniques are well-known and are, for example, described in U.S. Pat. No. 4,810,658. The use of such techniques enables the signal arising from fluorophores located very close to the surface of a waveguide to be distinguished from the signal arising from fluorophores contained within the bulk of the sample under assay thereby eliminating problems arising from optical interference from the sample.

The irradiation of the device must be such as to cause the immobilised species to exhibit its optical property e.g. fluorescence. The precise way of carrying out the irradiation will, however, depend upon the nature of the device. For a capillary fill type device, for example, the technique will generally involve irradiation of the measurement region of the waveguide at an angle at or near to 90° to the longitudinal axis of the waveguide, thereby exciting the species in that region. For a fibre-type waveguide, for example, the irradiation technique will generally involve propagation longitudinally in the fibre and subsequent excitation of the species in the measurement region. Such techniques and consideration of their applicability to the different types of devices available are well known to the person skilled in the art.

The optical property of the species measured may be, for example, the wavelength, intensity or polarisation of the fluorescent light emitted.

Preferred devices and methods according to the present invention are those in which the change in environment occurring as a result of the enzyme catalytic activity is a pH-change. The subsequent description is set out in terms of devices and methods of assay in which a pH-change occurs but the invention is not to be considered as being limited to such a change.

The device according to the invention will now be more particularly described with reference to embodiments of the invention wherein the immobilised species is a pH-sensitive fluorophore and the analyte under assay is an enzyme-substrate (and hence the device according to the invention has an enzyme immobilised thereon).

BRIEF DESCRIPTION OF THE DRAWINGS

FIG. 3a is a schematic illustration of the third embodiment of the device;

FIG. 3b illustrates the use of the device of FIG. 3a;

FIG. 4a is a schematic illustration of a fourth embodiment of an inventive device;

FIG. 4b is an illustration of an alternative calibration region;

FIG. 4c is an illustration of a device of FIG. 1a having two calibrational regions;

FIG. 4d is an illustration of a second calibration region;

FIG. 4e is an illustration of a third calibration region;

FIG. 4f is an illustration of a fourth calibration region;

FURTHER DESCRIPTION OF THE INVENTION

Figure 1A:
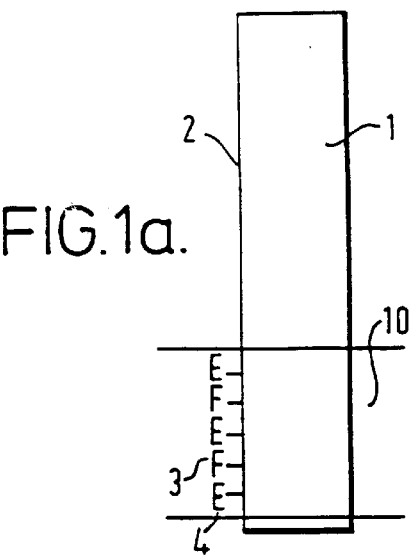
FIG. 1a is a schematic illustration of a first embodiment of the invented device.

In a device according to such an embodiment, the fluorophore and the enzyme may be directly or indirectly immobilised onto the surface of the waveguide in a number of ways. When directly immobilised, these components may either be immobilised separately onto the waveguide, or the fluorophore can be conjugated to the enzyme and the resulting conjugate may be immobilised onto the waveguide. Fluorophores may for example be immobilised by conventional coupling techniques. Enzymes and enzyme/fluorophore conjugates may be immobilised by conventional covalent coupling techniques or by suitable adsorption coupling techniques well-known to those skilled in the art. Indirect immobilisation may be achieved by the use of an intervening species bound to the waveguide, to which species the enzyme, fluorophore or enzyme/fluorophore conjugate is subsequently bound e.g. an antibody against the enzyme or avidin bound to the waveguide immobilising biotinylated enzyme.

A further example of an indirect immobilisation technique involves the use of a membrane permeable to the analyte under assay in which may be contained either enzyme and/or fluorophore or enzyme/fluorophore conjugate, the species not contained therein being immobilised to the waveguide as indicated above. Alternatively, the membrane may not contain any such species but may simply be laid over those species immobilised to the waveguide. In either case, the function of the membrane is to protect the enzyme from degradation by contaminants within the sample and also to minimise the effect of the buffering ability of the sample which would reduce the pH change caused by the catalytic activity of the enzyme.

As mentioned previously, for enzymes requiring a cofactor in order to bind their substrate and/or catalyse its breakdown into product, this cofactor can be initially present in or on the device in an appropriate amount in the vicinity of the measurement region. Alternatively, the required amount of cofactor can be added to the sample prior to incubation of the sample with the device or can be introduced into the sample once incubation has begun. Where cofactor is initially present this may be achieved, for example, by containing it within the membrane referred to above. Alternatively, it may, for example, be contained within a dissoluble layer of a suitable material in the measurement region either with or without the membrane referred to above being present. For a capillary-fill device of the type generally described in EP 171148, the cofactor may advantageously be contained in soluble releasable form within a zone on the measurement region (on one of the plates defining the region of sample containment) or alternatively within corresponding zone on the other plate such that on incubating the sample the cofactor is introduced into the vicinity of the measurement region.

The waveguide may be fabricated from a variety of materials, the only criterion regarding their selection being that they should be transparent to the wavelengths of light employed in the irradiation of the sensor and the wavelengths of the resulting propagated light from the surface of the waveguide. Suitable materials include glass, quartz and polymeric materials (such as polyacrylate).

The change in optical properties of the fluorophore may be measured by conventional methods for example, as described in U.S. Pat. No. 4,810,658 and in Badley et al, Philosophical Transactions of the Royal Society of London, Ser.B, Vol. 316, pp 143–160, 1987.

As mentioned hereinbefore, a wide variety of devices according to the invention may be envisaged. As described in International Patent Application No. PCT/GB91/02058, it is possible to contain within a sensor device, in addition to the measurement region, a number of distinct regions for the purposes of internal calibration. Such a principle can be applied to the sensor device according to the present invention.

Hence, according to one embodiment of the device according to the invention, the waveguide additionally has immobilised directly or indirectly on one or optionally more than one discrete region of said longitudinal surface, distinct from the measurement region, ("the calibration region(s)") further reagents suitable for the particular assay being performed, these further reagents being chosen such that in use, said reagents, together with optional ancillary reagents introduced into the sample during operation of assay and together with the analyte under assay, when present, give rise in said calibration region(s) to either i) a catalytic reaction analogous and preferably of enhanced or reduced extent to that in the measurement region, or ii) no catalytic reaction, or iii) a catalytic reaction which results in no detectable change in optical properties of any species present in said region.

Thus, according to an embodiment of the method of assay hereinbefore defined, the sample is incubated in the presence of a device according to the invention containing one or more calibration regions as hereinbefore defined; additionally including the step of monitoring an appropriate optical property ("the calibration signal(s)") thereby exhibited by the species in said calibration region(s) of said device and from the measurement signal and said calibration signal(s), using an appropriate algorithm, deriving a measure of the concentration of the analyte under assay.

Hence, in cases ii) or iii) in the embodiment of the device described above, the calibration region will correspond to a 'zero signal calibration region', using the terminology of International Patent Application No. PCT/GB91/02058. In case i) above where in the calibration region a reaction occurs analogous but of enhanced extent to that in the measurement region, the calibration region will correspond to a 'positive calibration region' using the terminology of International Patent Application No. PCT/GB91-02058. In case i) above where in the calibration region a reaction occurs analogous but of reduced extent to that in the measurement region, the calibration region will therefore, using similar terminology, correspond to a 'negative calibration region'.

According to a further aspect of the present invention, there is provided apparatus suitable for use in a method of assay as hereinbefore defined which comprises a device as hereinbefore defined; a source of radiation capable of being arranged such that, in use, radiation enters the said device such that the immobilised species whose optical properties change as a result of a change in environment in the device are excited; and means for monitoring the emerging radiation.

Specific embodiments of the device according to the present invention will now be described with reference to the accompanying drawings.

FIG. 1a illustrates schematically an embodiment of the device wherein the sensor is of the dipstick-type. Onto a region 10 of one longitudinal surface 2 of an optical waveguide 1 in the form of a glass sheet is immobilised an enzyme (E) 4 and a pH-sensitive fluorophore (F) 3.

Figure 1B:
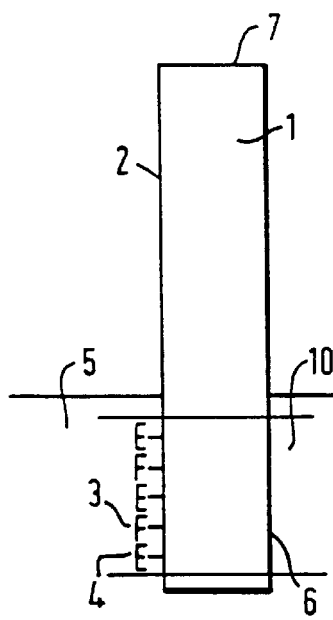
FIG. 1b is an illustration of the device of FIG. 1a in use.

FIG. 1b illustrates the device of FIG. 1a in use. In use, the device is dipped into the sample 5 which, if it contains the analyte of interest, being the substrate for the immobilised enzyme 4, the enzyme 4 will bind its substrate and catalyse its breakdown into product. The catalytic reaction results in a change in the pH in the local environment of the enzyme i.e. at the surface of the waveguide. This change in pH results in a change in the fluorescent properties of the immobilised fluorophore 3. From a radiation source 13, light of the appropriate wavelength (selected by means of suitable filters 14) to excite the fluorophore 3 falls onto the surface 6 of the waveguide and the propagated light originating from the end 7 of the waveguide is detected evanescently. The rate of change or the absolute change in the wavelength, intensity or polarisation of emitted fluorescence of the immobilised fluorophore 3 is measured and the activity of the immobilised enzyme 4 can thus be deduced. From this, the concentration of the enzyme-substrate, the analyte under assay, in the sample 5 can be determined.

Such a device may be calibrated by immersing it into solutions containing a known concentration of the analyte to be assayed. After a suitable incubation period, the fluorescence characteristics of the waveguide are measured and a standard curve of the measured signal versus analyte concentration can be constructed. The standard curve can then be employed to relate the measured signal under operation of the device to the concentration of the analyte under assay.

Figure 2A:
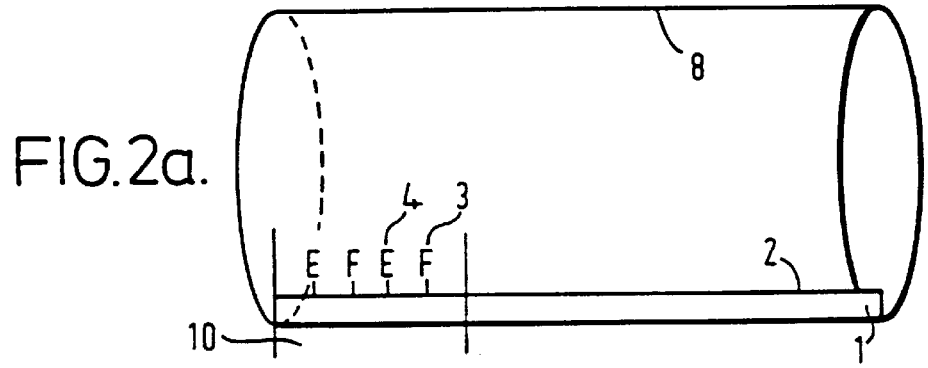
FIG. 2a is a schematic illustration of a second embodiment of the device.

FIG. 2a illustrates schematically an alternative embodiment of the device wherein the sensor may be employed to assay a flowing sample. The sensor, as described in FIG. 2a, forms part of the internal surface of a hollow structure having a cross-sectional shape suitable for the application of the assay, but preferably the portion 8 of the internal surface is substantially cylindrical. Onto a region 10 of one longitudinal surface 2 of an optical waveguide 1 is immobilised an enzyme (E) 4 and a pH-sensitive fluorophore (F) 3.

Figure 2B:
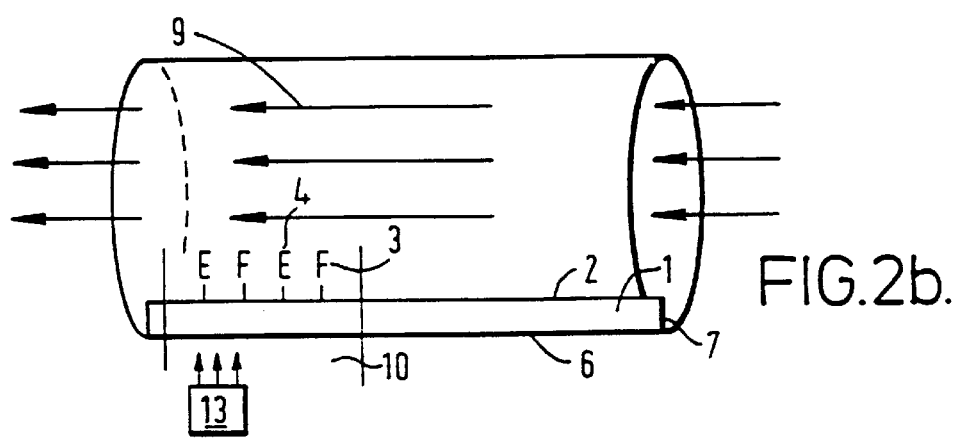
FIG. 2b is an illustration of the device of FIG. 2a in use.

The mode of operation of this embodiment of the device is essentially as described for the device shown in FIG. 1b. FIG. 2b illustrates the device of FIG. 2a in use. The advantage of this embodiment over the device of FIG. 1b is that it allows for the continuous monitoring of a flowing sample stream 9, in the path of which stream the device is placed. The sample stream may be periodically interrupted to allow for re-calibration of the device. This embodiment may advantageously be used in conjunction with other analytical techniques such as flow injection analysis and high performance liquid chromatography.

FIG. 3a illustrates schematically an alternative embodiment of the device wherein the sensor is a fluorescent capillary fill device (FCFD) of the type more generally described in EP 171148. Such a device comprises two flat plates separated by a capillary gap. The sensor consists of a lower optical waveguide 1 in the form of a glass sheet, onto a portion 10 of the longitudinal surface 2 of which is immobilised an enzyme 4 and a pH-sensitive fluorophore 3.

FIG. 3b illustrates the device of FIG. 3a in use. The sample 5 is introduced into the device or enters the device by capillarity. The mode of operation of the device is as described for the device illustrated in FIG. 1b.

FIG. 4a illustrates schematically an embodiment of the device in which a device in other respects similar to that of FIG. 1a additionally contains a calibration region 11 onto a portion of which is immobilised an enzyme (E) 4 and a pH-sensitive fluorophore (F) 3, the calibration region also carrying a layer comprising, in soluble releasable form, an amount of the enzyme-substrate (S) 15. In use, any reaction occurring in the measurement region 10 due to sample analyte presence will be analogous to that in the device of FIG. 1a. The reaction occurring in the calibration region 11 will be identical to that in region 10 but, due to the presence of additional enzyme substrate, will be of enhanced extent. Thus this region 11 will correspond to a positive calibration region.

FIG. 4b illustrates an alternative calibration region 11 which, in addition to having immobilised enzyme (E) and pH-sensitive fluorophore (F), thereon, carries a layer comprising, in soluble releasable form, an amount of an enzyme inhibitor (I) 16 specific to the enzyme E. Thus, in use, any reaction occurring in region 11 due to sample analyte presence will be of reduced extent as compared with that in the measurement region 10. Thus this region will correspond to a negative calibration region.

FIG. 4c illustrates schematically an embodiment of the device wherein the device of FIG. 1a additionally contains two calibration regions 11 and 12. Calibration region 11 contains those reagents described for the positive calibration region above. Onto a portion of calibration region 12 is immobilised inactivated enzyme (E') 17 (i.e. enzyme inactivated in the sense that it no longer binds to its substrate) and a pH-sensitive fluorophore (F) 3. Hence in use, no binding of enzyme 17 to its substrate occurs and therefore no catalytic reaction will occur in region 12. This region will therefore in use correspond to a zero signal calibration region. If instead enzyme 17 is inactivated in the sense that it binds to its substrate but does not catalyse its breakdown into product, in use this region will correspond to a negative calibration region. In the case of an enzyme requiring a cofactor, absence of the cofactor will give an analogous result to one or other of these possibilities.

FIG. 4d illustrates an alternative calibration region 12, onto which is immobilised a pH-sensitive fluorophore 3 alone i.e. no enzyme is present. This region in use will correspond to a zero signal calibration region.

FIG. 4e illustrates an alternative calibration region 12, onto which is immobilised an enzyme non-specific for the sample analyte (E") 18 and a pH-sensitive fluorophore (F) 3. This region in use will also correspond to a zero calibration region.

FIG. 4f illustrates an alternative calibration region 12, onto which is immobilised an enzyme (E) 4 and a non-pH sensitive fluorophore (F') 19. This region in use will also correspond to a zero signal calibration region.

Further embodiments of the device wherein the sensor is of the dipstick-type may be envisaged in which alternative combinations of the calibration regions 11 and 12 illustrated above are employed, or in which more than two calibration regions, selected from those illustrate above for regions 11 and 12, are employed.

Figure 5A:
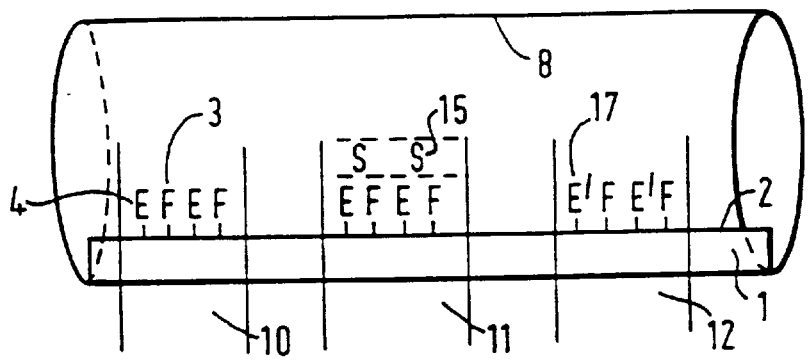
FIG. 5a is an illustration of a fifth calibration region.
Figure 5B:
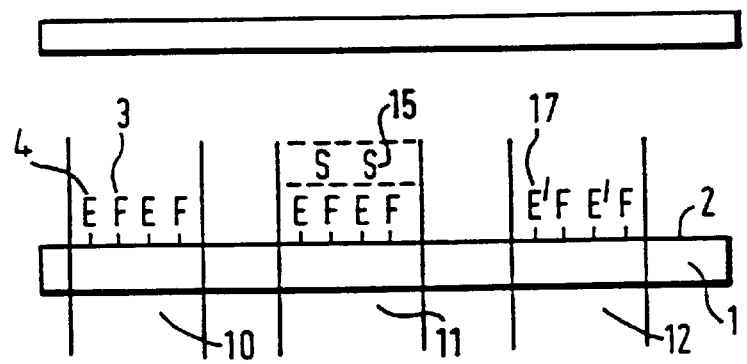
FIG. 5b is an illustration of a sixth calibration region.

Similarly, embodiments of the device wherein the devices of FIGS. 2a and 3a contain analogous additional calibration regions may be envisaged. FIGS. 5a and 5b illustrate two such embodiments.

Figure 6:
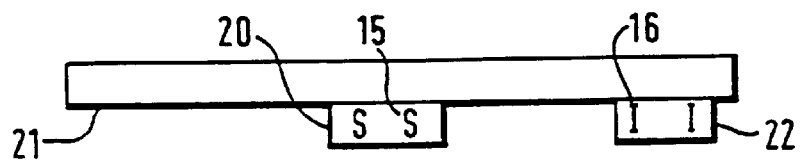
FIG. 6 is an illustration of a fluorescent capillary device and center arrangement.
Figure 6:
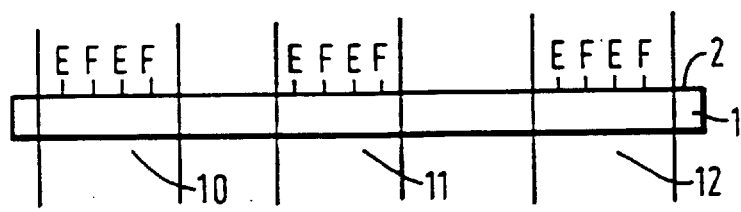

FIG. 6 illustrates an embodiment of the device wherein the sensor is a fluorescent capillary device containing in addition to the measurement region 10 two calibration regions 11 and 12, onto each of which is immobilised an enzyme (E) 4 and a pH-sensitive fluorophore (F) 3. On a region 20 of the top plate 21 of the device is carried a layer of enzyme substrate (S) 15 in soluble releasable form. On a region 22 of the top plate 21 of the device is carried a layer of enzyme inhibitor (I) 16 in soluble releasable form. In use, when sample enters the cavity within the device, reagents 15 and 16 dissolve and diffuse towards regions 11 and 12 respectively. Hence in region 11 an enhanced reaction occurs compared to that in region 10 and in region 12 a reduced reaction occurs compared to that in region 10, Region 11 in use is thus a positive calibration region and region 12 in use is thus a negative calibration region.

The following non-limiting Example serves to further illustrate the present invention.

EXAMPLE 1

Optical Glucose Sensor 1.1 Preparation of fluorophore- and enzyme-coated waveguides A sheet of Permabloc glass (Pilkington Glass Ltd., St. Helens, UK) having a thickness of about 1 mm was cleaned with detergent (e.g. Tween 20) in ultra-pure water with ultrasonic agitation. The surface of the glass was activated by incubating it in a 2% solution of aminopropyltriethoxysilane in water at a pH of 3 to 4 for two hours at 75° C. After rinsing in water, the glass sheet was dried at 115° C. for at least four hours. The glass was then incubated for 60 minutes in a 2.5% solution of glutaraldehyde in a 0.05M phosphate buffer (pH 7), and then washed thoroughly with distilled water. The glass was incubated for two to four hours in a 1% solution of a glucose oxidase (EC 1.1.3.4) in phosphate buffer (pH 7). The glass sheet was then washed with buffer solution. Unwanted adsorbed protein was removed by soaking with a 6M urea solution in known manner. The glass sheet was then incubated with a 1% solution of FITC, followed by a wash step. This formed plate 1 of the FCFD test device as illustrated in FIGS. 3a and 3b.

1.2 Fabrication of FCFD test devices

Test devices such as have been described in EP-A-0171148 were fabricated by screen printing onto the waveguide resulting from step 1.1 above bonding tracks of an ultraviolet curing glue (UVS 91, Norland Inc., USA) containing glass microspheres of diameter 100 $\mu$m diameter (Jencons Ltd., UK). A sheet of Permabloc glass onto which had been screen printed opaque lids as described in WO90/14590 was then placed over the waveguide, and a vacuum applied to the laminate. As result of the vacuum, the upper sheet of glass was caused to press down onto the glue, the glass microspheres defining a gap of 100 $\mu$m between the glass sheets. The laminate was then exposed to an ultraviolet light source to cure the glue. Finally, the laminate sheet was broken into individual test devices as described in EP-A-0171148.

1.3 Apparatus Used in the Measurement of the Glucose Assay

Figure 7:
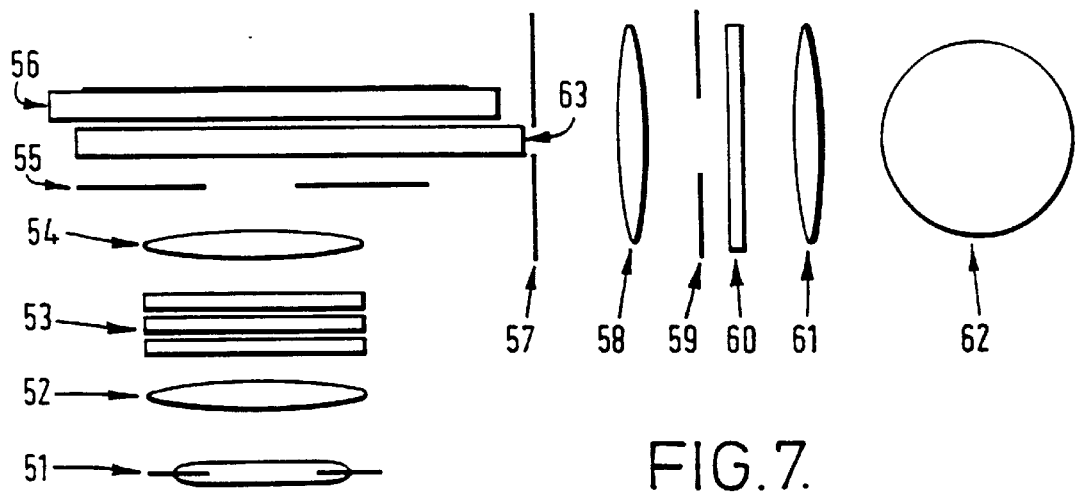
FIG. 7 is an illustration of a fluorimetry apparatus.

FIG. 7 shows a simple fluorimetry apparatus which was used to make suitable assay measurements as described in GB8911462.3. Light from a xenon flash lamp 51 (Heinmann) is roughly collimated by a lens 52 before passing through a filter stack 53 which defines the wavelength range used to excite the FITC. The filter stack comprises three filters:

a BG7 Schott glass filter (Ealing Electro Optics UK Ltd., Watford, UK), a 450–480 nm FITC bandpass interference filter (Optometrics Ltd., UK), a 474 nm shortpass interference filter (Comar Instruments Ltd., Cambridge, UK).

A second lens 54 focuses the excitation light onto the active surface of the FCFD 56 through an aperture 55. Light emitted from the optical edge 63 of the FCFD passes through an aperture 57 which prevents light emitted directly out of the solution contained within the FCFD 56 entering the detection optics.

A lens system 58 collects the emitted light and an aperture 59 defines the angular range over which the emission is measured. This was chosen to coincide with angles associated with evanescently coupled fluorescence emission. A Schott OG515 515 nm colloidal glass longpass filter 60 (Ealing Electro Optics UK Ltd., Watford, UK) filters out any scattered pump light and a second lens 61 focuses the emission onto a photomultiplier detector (Hamamatsu R931A, Hakuto UK Ltd) 62.

1.4 Assay procedure for glucose

Figure 8:
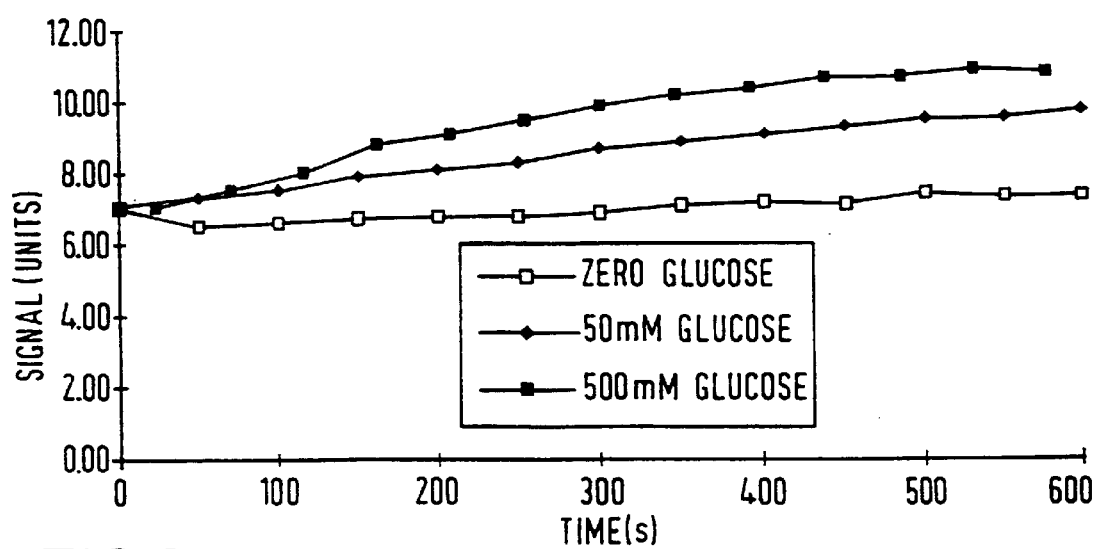
FIG. 8 is a graph of the change in signal with increasing concentration.

Buffer solutions (0.05M phosphate, pH 7) containing various concentrations of glucose were prepared. Either buffer solutions containing no glucose or buffer solutions containing glucose were added to the FCFD and the change of signal arising from the device was monitored with time. As the immobilised enzyme catalysed the breakdown of glucose, the pH within the device altered, changing the activity of the immobilised FITC. FIG. 8 shows the change in signal arising from the FITC with increasing concentrations of glucose within the device.

We claim:

1. A sensor device for use in an assay for an analyte substance selected from the group consisting of (i) an enzyme capable of producing a change in its environment as a result of catalytic reaction with a substrate and (ii) said substrate, which sensor device possesses at least one cavity having a dimension small enough to enable sample liquid to be drawn into the cavity by capillary action, wherein a surface of the cavity has immobilised directly or indirectly on a measurement region which is a discrete region said surface a fluorophore species whose optical properties change as a result of said change in environment together with the enzyme substrate or enzyme pair complementary to said substance, and wherein said surface is a surface of a transparent solid plate light-transmissive waveguide and which forms a wall of the cavity, and wherein the waveguide additionally has immobilised directly or indirectly on at least one calibration region which is a discrete region of said surface distinct from the measurement region, a further reagent which together with analyte present gives rise in said calibration region to i) a catalytic reaction analogous to that in the measurement region, or ii) no catalytic reaction, or iii) a catalytic reaction which results in no detectable change in optical properties of any species present in said region.

2. A sensor device as claimed in claim 1 in which said enzyme requires a cofactor for said catalytic reaction to occur and said cofactor is additionally present in or on the device.

3. A device as claimed in claim 1 wherein the enzyme is such that said change in environment as a result of the catalytic reaction of the enzyme with a substrate is a change in pH.

4. A device as claimed in claim 1 including a source of radiation capable of being arranged such that radiation enters the device such that the immobilised species whose optical properties change as a result of a change in environment in the device are excited and radiation emerges; and a monitor for the emerging radiation.

5. A device as claimed in claim 4 wherein said further reagent together with the analyte present can give rise in said calibration region to a catalytic reaction of enhanced or reduced extent to that in the measurement region.

6. A device as claimed in claim 5 wherein the enzyme is such that the said change in environment as a result of the catalytic reaction of the enzyme with a substrate is a change in pH.

7. A device as claimed in claim 4 wherein said source of radiation is disposed such that radiation enters the device normal to said surface.

8. A kit for performing a method of assay comprising a device as claimed in claim 1 together with ancillary reagents.

9. A method of assay for an analyte which is an enzyme or an enzyme substrate in a sample which method includes the steps of:

(a) incubating the sample in the presence of a device as claimed in claim 1;
 (b) irradiating the device;
 (c) monitoring a measurement signal which is an optical property measurement signal exhibited by the fluorophore species in said measurement region of said device;
 (d) determining the extent to which or the rate at which said optical property is altered by any change in the environment in said measurement region or both; and
 (e) comparing the extent to which or the rate at which said optical property is altered by any change in the environment in said measurement region to a corresponding change in the environment in said measurement region, wherein said corresponding change is caused by any interaction of enzyme and enzyme substrate and thereby deriving a measure of the concentration of the analyte.

10. A method as claimed in claim 9 wherein a calibration signal which is an optical property thereby exhibited by the species in said calibration region of said device and from the measurement signal and said calibration signal deriving a measure of the concentration of the analyte is monitored.

11. A method as claimed in claim 9 wherein said irradiation is such that radiation enters the device normal to said surface.

* * * * *